US008884613B2

(12) United States Patent
Fujita (10) Patent No.: US 8,884,613 B2
(45) Date of Patent: Nov. 11, 2014

(54) WATER-CHAMBER WORKING APPARATUS

(75) Inventor: Jun Fujita, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 366 days.

(21) Appl. No.: 13/517,180

(22) PCT Filed: Jan. 19, 2011

(86) PCT No.: PCT/JP2011/050890
§ 371 (c)(1),
(2), (4) Date: Jun. 19, 2012

(87) PCT Pub. No.: WO2011/093191
PCT Pub. Date: Aug. 4, 2011

(65) Prior Publication Data
US 2012/0255289 A1    Oct. 11, 2012

(30) Foreign Application Priority Data

Jan. 27, 2010  (JP) ................................ 2010-015864

(51) Int. Cl.
| | | |
|---|---|---|
| *G01N 27/72* | (2006.01) | |
| *G01R 33/12* | (2006.01) | |
| *G21C 17/017* | (2006.01) | |
| *F22B 37/00* | (2006.01) | |
| *G21D 1/00* | (2006.01) | |

(52) U.S. Cl.
CPC ................ *G21C 17/017* (2013.01); *G21D 1/00* (2013.01); *G21D 1/006* (2013.01); *G01R 33/12* (2013.01); *G01N 27/72* (2013.01); *Y02E 30/40* (2013.01); *F22B 37/003* (2013.01)
USPC ........... 324/228; 324/233; 324/234; 324/235; 324/236; 324/237; 324/238; 324/239; 324/240; 324/241; 324/242; 324/243

(58) Field of Classification Search
CPC ......... G01N 27/72; G01R 33/12; G21D 1/00; F22B 37/003; G21C 17/017; Y02E 30/40
USPC .......................................... 324/228, 233–243
See application file for complete search history.

(56) References Cited

U.S. PATENT DOCUMENTS 4,148,403 A * 4/1979 Riffe ................................. 414/2
4,158,415 A * 6/1979 Young .............................. 414/2
(Continued)

FOREIGN PATENT DOCUMENTS

| JP | 56-138298 A | 10/1981 |
|---|---|---|
| JP | 64-23389 U | 2/1989 |

(Continued)

OTHER PUBLICATIONS

Decision of a Patent Grant dated Jun. 11, 2013, issued in corresponding Japanese Patent Application No. 2010-015864, with partial translation.

(Continued)

*Primary Examiner* — Patrick Assouad
*Assistant Examiner* — Lamarr Brown
(74) *Attorney, Agent, or Firm* — Westerman, Hattori, Daniels & Adrian, LLP (57) ABSTRACT

A water-chamber working apparatus 1 according to the present invention includes a movable body that can move along a tube plate 12 of a steam generator 10, an extendable member 21 that extends and retracts in a direction in which a first coupling portion 21*d* approach each other and a direction in which these portions move away from each other, where the first coupling portion 21*d* is attached to a maintenance hatch 15 via a first joint 23*a* including two rotation axes intersecting with each other, and the second coupling portion 21*e* is attached to the movable body via a second joint 23*b* including two rotation axes intersecting with each other, which are different from the rotation axes of the first joint 23*a*.

12 Claims, 8 Drawing Sheets

(56) References Cited

U.S. PATENT DOCUMENTS

| | | | | |
|---|---|---|---|---|
| 4,168,782 | A | * | 9/1979 | Sturges, Jr. ....................... 414/4 |
| 4,193,735 | A | * | 3/1980 | Savor et al. ................. 414/749.4 |
| 4,231,690 | A | * | 11/1980 | Burns ............................. 408/80 |
| 4,231,696 | A | * | 11/1980 | Rieben .............................. 414/5 |
| 4,262,402 | A | * | 4/1981 | Cooper et al. ........... 29/890.121 |
| 4,287,655 | A | * | 9/1981 | Gerkey et al. ............ 29/890.031 |
| 4,303,368 | A | * | 12/1981 | Dent et al. .................... 414/590 |
| 4,425,296 | A | * | 1/1984 | Adamowski et al. ......... 376/245 |
| 4,438,805 | A | * | 3/1984 | Gugel .......................... 165/11.2 |
| 4,561,816 | A | * | 12/1985 | Dingess ............................ 414/4 |
| 4,804,038 | A | * | 2/1989 | Klahn et al. ................. 165/11.2 |
| 4,924,933 | A | * | 5/1990 | Richter et al. ................... 165/76 |
| 4,942,545 | A | * | 7/1990 | Sapia .............................. 702/97 |
| 4,954,312 | A | * | 9/1990 | McDonald et al. ........... 376/260 |
| 4,984,598 | A | * | 1/1991 | Gemma .................... 134/166 R |
| 4,984,627 | A | * | 1/1991 | LeBourgeois ............... 165/11.2 |
| 5,037,215 | A | * | 8/1991 | Crick ...................... 400/124.01 |
| 5,178,820 | A | * | 1/1993 | Glass et al. ................... 376/260 |
| 5,265,667 | A | * | 11/1993 | Lester et al. ................. 165/11.2 |
| 5,291,136 | A | * | 3/1994 | Van der Veer et al. ........ 324/262 |
| 5,355,063 | A | * | 10/1994 | Boone et al. ............. 318/568.11 |
| 5,751,610 | A | * | 5/1998 | Gan et al. ....................... 700/85 |
| 6,040,695 | A | * | 3/2000 | Raulerson et al. ............ 324/240 |
| 6,414,480 | B1 | * | 7/2002 | Traxler ......................... 324/202 |
| 7,368,907 | B2 | * | 5/2008 | Raulerson et al. ............ 324/238 |
| 7,436,992 | B2 | * | 10/2008 | Suh et al. ...................... 382/141 |
| 7,533,715 | B1 | * | 5/2009 | Klahn et al. ................. 165/11.2 |
| 7,690,234 | B2 | * | 4/2010 | Mori et al. ....................... 72/53 |
| 2008/0223106 | A1 | * | 9/2008 | Mori et al. ...................... 72/462 |
| 2009/0115410 | A1 | * | 5/2009 | McKnight et al. ............ 324/240 |
| 2009/0120605 | A1 | * | 5/2009 | Klahn et al. ................. 165/11.2 |

FOREIGN PATENT DOCUMENTS

| | | |
|---|---|---|
| JP | 10-227765 A | 8/1998 |
| JP | 2007-181909 A | 7/2007 |
| WO | 2009/113398 A1 | 9/2009 |

OTHER PUBLICATIONS

International Search Report of PCT/JP2011/050890, date of mailing Mar. 1, 2011.

Translation of Japanese Written Opinion of PCT/JP2011/050890, mailing date Mar. 1, 2011, which was previously submitted on Jul. 13, 2012.

* cited by examiner

WATER-CHAMBER WORKING APPARATUS

FIELD

The present invention relates to a water-chamber working apparatus that performs a predetermined work in a water chamber of a steam generator.

BACKGROUND

As for a work in a water chamber of a steam generator provided in a nuclear plant, it is desired that the workload of workers is reduced. Therefore, conventionally, there is a technique of performing a work in a water chamber by introducing a water-chamber working apparatus into the water chamber and remote-controlling the water-chamber working apparatus. For example, Patent Literature 1 discloses a remote testing apparatus that performs flaw testing of a number of heat transfer tubes of a steam generator.

CITATION LIST

Patent Literature

Patent Literature 1: Japanese Patent Application Laid-open No. H10-227765

SUMMARY

Technical Problem

According to the technique disclosed in Patent Literature 1, as shown in FIG. 2 thereof, a clamp shaft is inserted into a plurality of heat transfer tubes provided in the steam generator, thereby supporting a walking guide robot on a tube plate of the stream generator. That is, according to the technique disclosed in Patent Literature 1, the walking guide robot is suspended from the tube plate. In the following explanations, a device that moves along a tube plate like the walking guide robot in the technique disclosed in Patent Literature 1 is referred to as "movable body". In a water-chamber working apparatus in which a movable body is suspended from a tube plate, it is designed so that the movable body does not fall from the tube plate, and remote control is performed carefully so that the movable body does not fall from the tube plate. In this way, when the movable body is suspended from the tube plate, designing of the movable body may become complicated or working hours may increase for carefully performing remote control of the movable body, in order to cause the movable body to follow the tube plate stably.

The present invention has been achieved in view of the above problems, and an object of the present invention is to provide a water-chamber working apparatus that can stably support a movable body on a tube plate.

Solution to Problem

According to an aspect of the present invention, a water-chamber working apparatus that performs a predetermined work inside a water chamber of a steam generator includes: a movable body that is configured to move along a tube plate of the steam generator; an extendable member that includes a first portion and a second portion and that extends and retracts in a direction in which the first portion and the second portion approach each other and a direction in which theses portions move away from each other, where the first portion is attached to a portion of the water chamber that is away from the tube plate via a first joint including two rotation axes intersecting with each other, and the second portion is attached to the movable body via a second joint including two rotation axes intersecting with each other, which are different from the rotation axes of the first joint; a first force application unit that applies a force in a direction in which the first portion and the second portion move away from each other to the extendable member; and a second force application unit that applies a force of rotating the extendable member centering around the first joint, which is a force to cause the second portion to approach to the tube plate, to the extendable member.

According to the above configuration, a force in a direction in which the movable body itself approaches the tube plate is transmitted to the movable body according to the present invention via the extendable member, by a force generated by the first force application unit and the second force application unit. With this configuration, the movable body according to the present invention is pressed against the tube plate. Accordingly, the movable body can move stably along the tube plate without being suspended from the tube plate.

Advantageously, in the water-chamber working apparatus, the second force application unit includes an electric motor, and a counterweight mechanism including a rod-like member for weight that is extended to a direction opposite to the second portion while using the first portion as a fulcrum, and a weight provided in a portion of the rod-like member for weight that is away from the first portion.

By providing both the electric motor and the counterweight mechanism, the counterweight mechanism can decrease the magnitude of a force to be applied to the extendable member by the electric motor. Furthermore, the electric motor can decrease the magnitude of a force to be applied to the extendable member by the counterweight mechanism. With this configuration, the electric motor can be further downsized in the water-chamber working apparatus according to the present invention by providing both the electric motor and the counterweight mechanism in the water-chamber working apparatus as compared to a case of providing only the electric motor, because an output required for the electric motor is reduced. Further, in the water-chamber working apparatus according to the present invention, the mass of the weight can be further decreased or a distance between the weight and the first portion can be further decreased by providing both the electric motor and the counterweight mechanism in the water-chamber working apparatus as compared to a case of providing only the counterweight mechanism.

Advantageously, in the water-chamber working apparatus, the electric motor increases the force to be applied to the extendable member as a distance between the first portion and the second portion increases, and decreases the force to be applied to the extendable member as the distance between the first portion and the second portion decreases.

As the distance between the first portion and the second portion increases, a force required to be generated by the second force application unit increases. Therefore, in the water-chamber working apparatus according to the present invention, as the distance between the first portion and the second portion increases, the force to be applied to the extendable member by the electric motor is increased. On the other hand, as the distance between the first portion and the second portion decreases, the force required to be generated by the second force application unit is decreased. Therefore, in the water-chamber working apparatus according to the present invention, as the distance between the first portion and the second portion decreases, the force to be applied to the extendable member by the electric motor is decreased. Consequently, the water-chamber working apparatus according to the present invention can bring a force acting on the movable body close to an appropriate value.

Advantageously, in the water-chamber working apparatus, the second force application unit is a counterweight mechanism including a rod-like member for weight that is extended to a direction opposite to the second portion while using the first portion as a fulcrum, and a weight provided in a portion of the rod-like member for weight that is away from the first portion.

The counterweight mechanism can apply a force to the extendable member without requiring any electricity. As a result, the water-chamber working apparatus according to the present invention can support the movable body on the tube plate stably without requiring any electricity.

Advantageously, in the water-chamber working apparatus, the rod-like member for weight extends and retracts in a direction in which the first portion and the weight approach each other and a direction in which the first portion and the weight move away from each other, and the water-chamber working apparatus comprises an arm-length adjustment unit that adjusts a distance between the first portion and the weight so that the distance between the first portion and the weight increases as a distance between the first portion and the second portion increases, and adjusts a distance between the first portion and the weight so that the distance between the first portion and the weight decreases as the distance between the first portion and the second portion decreases.

By the above configuration, the water-chamber working apparatus according to the present invention can adjust the distance between the first portion and the weight. As the distance between the first portion and the second portion increases, a force required to be generated by the second force application unit increases. Therefore, the water-chamber working apparatus according to the present invention increases the distance between the first portion and the weight, as the distance between the first portion and the second portion increases. With this configuration, the water-chamber working apparatus according to the present invention can increase a force to be applied to the movable body by the second force application unit, which is a force in a direction in which the movable body approaches the tube plate. On the other hand, as the distance between the first portion and the second portion decreases, the force required to be generated by the second force application unit decreases. Therefore, as the distance between the first portion and the second portion decreases, the water-chamber working apparatus according to the present invention decreases the distance between the first portion and the weight. With this configuration, the water-chamber working apparatus according to the present invention can decrease the force to be applied to the movable body by the second force application unit, which is a force in the direction in which the movable body approaches the tube plate. Therefore, the water-chamber working apparatus according to the present invention can bring a force acting on the movable body close to an appropriate value.

Advantageously, in the water-chamber working apparatus, the weight moves along the rod-like member for weight in a direction in which the weight approaches the first portion and a direction in which the weight moves away from the first portion, and the water-chamber working apparatus comprises a weight movement unit that moves the weight in a direction in which the weight moves away from the first portion as a distance between the first portion and the second portion increases, and moves the weight in a direction in which the weight approaches the first portion as the distance between the first portion and the second portion decreases.

By the above configuration, the water-chamber working apparatus according to the present invention can adjust the distance between the first portion and the weight.

Advantageously, in the water-chamber working apparatus, the weight is configured to include a container and liquid stored in the container, and the water-chamber working apparatus comprises a liquid-amount adjustment unit that increases an amount of the liquid in the container as a distance between the first portion and the second portion increases, and decreases an amount of the liquid in the container as the distance between the first portion and the second portion decreases.

By the above configuration, the water-chamber working apparatus according to the present invention increases the mass of the container containing liquid, as the distance between the first portion and the second portion increases. With this configuration, the water-chamber working apparatus according to the present invention can increase the force to be applied to the movable body by the second force application unit, which is a force in the direction in which the movable body approaches the tube plate. On the other hand, the water-chamber working apparatus according to the present invention decreases the mass of the container containing liquid, as the distance between the first portion and the second portion decreases. With this configuration, the water-chamber working apparatus according to the present invention can decrease the force to be applied to the movable body by the second force application unit, which is a force in the direction in which the movable body approaches the tube plate. Therefore, the water-chamber working apparatus according to the present invention can bring a force acting on the movable body close to an appropriate value.

Advantageously, in the water-chamber working apparatus, the second force application unit is an electric motor.

While the counterweight mechanism requires the rod-like member for weight, the electric motor does not require any rod-like member. Therefore, the water-chamber working apparatus according to the present invention can possibly further downsize the entire apparatus when including only the electric motor as compared to a case of including the counterweight mechanism, because the rod-like member can be omitted.

Advantageously, in the water-chamber working apparatus, the first force application unit is an extension device capable of adjusting an amount of extension and retraction, and adjusts a length of the extendable member by following a movement of the movable body.

For example, the extension device is a cylinder device or an actuator device. The water-chamber working apparatus according to the present invention detects a position of the movable body, and controls operations of the extension device so that the length of the extendable member becomes long, as the movable body moves away from the first portion. Furthermore, the water-chamber working apparatus controls operations of the extension device so that the length of the extendable member becomes short, as the movable body approaches the first portion. In this case, for example, when the movable body attempts to move against a force applied to the movable body by the first force application unit, the first force application unit decreases the length of the extendable member, so that the movable body can move easily.

As a preferred mode of the present invention, it is desired that the movable body performs, as a predetermined work, Eddy-current testing for probing a flaw formed in a heat transfer tube provided in the steam generator.

As a preferred mode of the present invention, it is desired that the movable body clamps the heat transfer tube.

When the water-chamber working apparatus performs Eddy-current testing, the movable body receives a force in a direction in which the movable body itself moves away from the heat transfer tube (a reaction force) from a probe. Therefore, when the movable body does not clamp the heat transfer tube, in the water-chamber working apparatus, the second force application unit needs to create a force against the reaction force. However, when the movable body clamps the heat transfer tube, the movable body is fixed to the tube plate by the clamping the heat transfer tube. Accordingly, in the water-chamber working apparatus according to the present invention, the second force application unit does not need to create a force against the reaction force.

Advantageous Effects of Invention

The water-chamber working apparatus can stably support a movable body on a tube plate.

DESCRIPTION OF EMBODIMENTS

The present invention is explained below in detail with reference to the accompanying drawings. The present invention is not limited to the following explanations. In addition, constituent elements in the following descriptions include those that can be easily assumed by persons skilled in the art, that are substantially equivalent, and so-called equivalents.

(First Embodiment)

Figure 1:
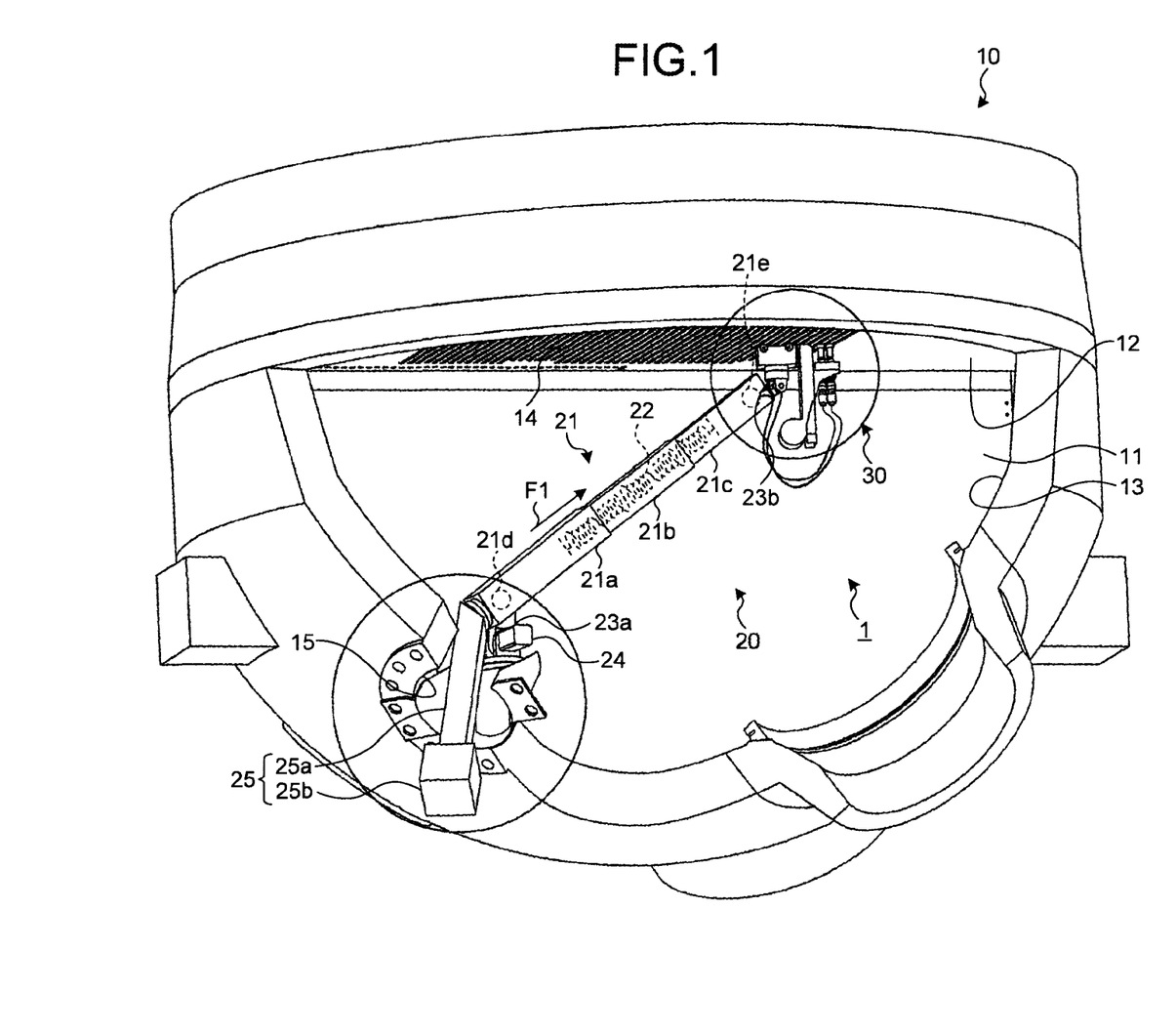
FIG. 1 is a perspective view of an entirety of a water-chamber working apparatus according to a first embodiment.

FIG. 1 is a perspective view of an entirety of a water-chamber working apparatus according to a first embodiment. As shown in FIG. 1, a steam generator 10 has a water chamber 11. The water chamber 11 is a space enclosed by a tube plate 12 and a hemispherical wall surface 13. The tube plate 12 is arranged vertically above the hemispherical wall surface 13. The tube plate 12 is provided substantially horizontally, for example. A plurality of heat transfer tubes 14 open in the tube plate 12. A maintenance hatch 15 connecting the inside and outside of the water chamber 11 is formed on the hemispherical wall surface 13. A water-chamber working apparatus 1 according to the present embodiment shown in FIG. 1 performs a predetermined work in the water chamber 11. In the present embodiment, it is assumed that the predetermined work is Eddy-current testing (ECT) as an example. The Eddy-current testing is a work of probing a flaw formed in the heat transfer tube 14. As shown in FIG. 1, the water-chamber working apparatus 1 includes a movable-body support device 20 and a flaw detector 30.

Figure 2:
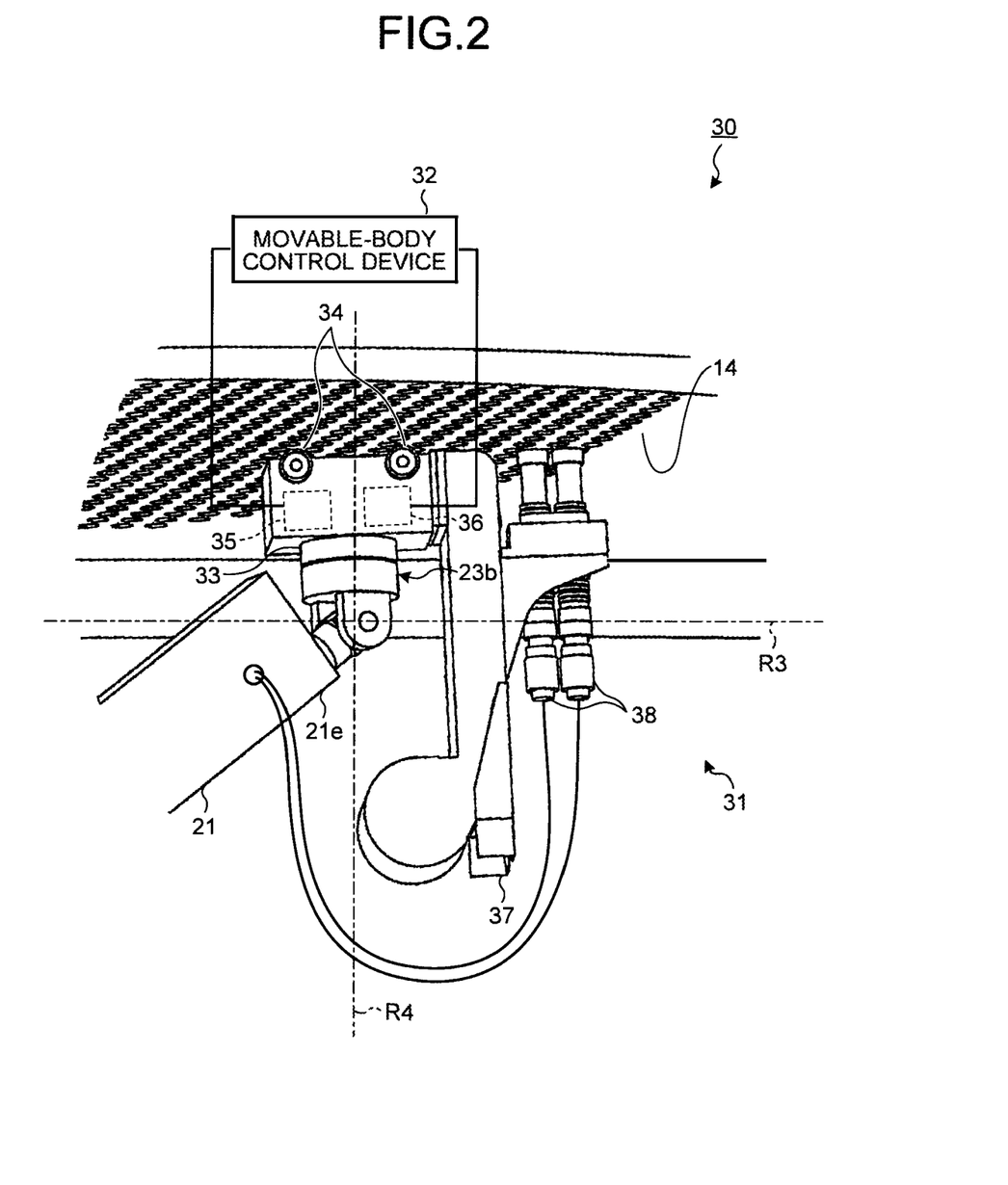
FIG. 2 is an enlarged perspective view of a vicinity of a movable body provided in a flaw detector according to the first embodiment.

FIG. 2 is an enlarged perspective view of a vicinity of a movable body provided in the flaw detector according to the first embodiment. As shown in FIG. 2, the flaw detector 30 includes a movable body 31 and a movable-body control device 32. An example of the configuration of the movable body 31 is explained below. The movable body 31 includes a frame 33, a wheel 34, a running electric motor 35, a running-direction-changing electric motor 36, and a probe support body 37. The wheel 34 is attached to the frame 33 so as to be able to rotate on a wheel axle. The wheel 34 is supported by the frame 33 so that an angle of the wheel axle with respect to the frame 33 can be changed on a virtual plane parallel to the tube plate 12.

The running electric motor 35 applies a rotative force centering around the wheel axle to the wheel 34. The running-direction-changing electric motor 36 adjusts an angle of the wheel axle with respect to the frame 33 on the virtual plane parallel to the tube plate 12. The probe support body 37 is attached to the frame 33. A probe 38 for Eddy-current testing is attached to the probe support body 37 and the probe support body 37 supports the probe 38 with respect to the frame 33. The probe 38 moves along the tube plate 12 together with the frame 33 due to the rotation of the wheel 34 in a state of contacting with the tube plate 12.

The movable-body control device 32 controls operations of the movable body 31. Specifically, the movable-body control device 32 is electrically coupled with the running electric motor 35, the running-direction-changing electric motor 36, and other movable devices to control operations of these movable bodies. When performing Eddy-current testing, first, the movable-body control device 32 controls operations of the running electric motor 35 and the running-direction-changing electric motor 36 so that the heat transfer tube 14 to be subjected to the Eddy-current testing and the probe 38 face each other, and moves the frame 33. For example, the movable-body control device 32 regulates rotation of a rotor of the running electric motor 35 to regulate rotation of the wheel 34, or inserts a rod-like member coupled with the frame 33 into another heat transfer tube 14 different from the heat transfer tube 14 to be subjected to the Eddy-current testing, thereby regulating the movement of the frame 33 along the tube plate 12. In this state, the flaw detector 30 performs the Eddy-current testing. When the Eddy-current testing of the heat transfer tube 14 as a current testing target is complete, the movable-body control device 32 controls operations of the running electric motor 35 and the running-direction-changing electric motor 36 so that the heat transfer tube 14 to be subjected to the Eddy-current testing next and the probe 38 face each other, and moves the frame 33 of the movable body 31. The flaw detector 30 repeats the above operations until the Eddy-current testing is performed on all the heat transfer tubes 14.

A configuration of the movable-body support device 20 is explained next. The movable-body support device 20 includes an extendable member 21, an extrusion spring 22 as a first force application unit, a first universal joint 23a as a first joint, a second universal joint 23b as a second joint, and a supporting electric motor 24 as a second force application unit. The extendable member 21 shown in FIG. 1 is a rod-like member. The extendable member 21 extends and retracts in a direction of a central axis of the rod-like member (a longitudinal direction of the rod-like member). A mechanism for extending and retracting the extendable member 21 is not particularly limited. For example, the extendable member 21 includes a hollow first rod-like member 21*a*, a hollow second rod-like member 21*b*, and a third rod-like member 21*c*. At least a part of the third rod-like member 21*c* is accommodated in a hollow part of the second rod-like member 21*b*, and the third rod-like member 21*c* can move in the direction of the central axis of the extendable member 21 with respect to the second rod-like member 21*b*. At least a part of the second rod-like member 21*b* is accommodated in a hollow part of the first rod-like member 21*a*, and the second rod-like member 21*b* can move in the direction of the central axis of the extendable member 21 with respect to the first rod-like member 21*a*.

Accordingly, the extendable member 21 extends and retracts by an amount of increase and decrease of the part of the second rod-like member 21*b* protruding from the hollow part of the first rod-like member 21*a*. Furthermore, the extendable member 21 extends and retracts by an amount of increase and decrease of the part of the third rod-like member 21*c* protruding from the hollow part of the second rod-like member 21*b*. In the extendable member 21, a first coupling portion 21*d* as a first portion is coupled with the maintenance hatch 15 of the steam generator 10 via the first universal joint 23*a*, and a second coupling portion 21*e* as a second portion is coupled with the frame 33 of the movable body 31 via the second universal joint 23*b*. The first coupling portion 21*d* is a part of the first rod-like member 21*a*, and in the present embodiment, is an end of the first rod-like member 21*a* on a side of the maintenance hatch 15. The second coupling portion 21*e* is a part of the third rod-like member 21, and in the present embodiment, it is an end of the third rod-like member 21*c* on a side of the tube plate 12.

The extrusion spring 22 is coupled with the first rod-like member 21*a* at one end, and with the third rod-like member 21*c* at the other end. Accordingly, the extrusion spring 22 applies a force F1 to the extendable member 21 in a direction in which the first coupling portion 21*d* and the second coupling portion 21*e* move away from each other. The first coupling portion 21*d* does not move with respect to the maintenance hatch 15, but the second coupling portion 21*e* moves with respect to the first coupling portion 21*d*. Accordingly, the extrusion spring 22 practically applies the force F1 to the extendable member 21 so that the extrusion spring 22 pushes the second coupling portion 21*e* to move away from the first coupling portion 21*d*. The water-chamber working apparatus 1 can be provided with an extension device that can adjust an extension amount thereof as the first force application unit instead of the extrusion spring 22. The extension device is, for example, a cylinder device or an actuator device that uses gas or liquid as a working fluid. In the case of the extrusion spring 22, the magnitude of the force F1 to be generated is changed according to the extension amount of the extendable member 21. On the other hand, in the extension device, there is an effect that the magnitude of the force F1 to be generated is less likely to be changed, even when the extension amount of the extendable member 21 changes.

Furthermore, when the first force application unit is the extension device, the extension device can be controlled such that the length of the extendable member 21 is changed, following the movement of the movable body 31. Specifically, the movable-body support device 20 detects the position of the movable body 31, and controls operations of the extension device so that the length of the extendable member 21 becomes longer, as the movable body 31 moves away from the first coupling portion 21*d*. Further, the movable-body support device 20 controls operations of the extension device so that the length of the extendable member 21 becomes shorter, as the movable body 31 approaches the first coupling portion 21*d*. In this case, for example, when the movable body 31 is to move against the force F1, the extension device shortens the length of the extendable member 21. Accordingly, the movable body 31 can move more easily. However, the extrusion spring 22 generally has a small mass and is smaller than the extension device. Further, operations of the extrusion spring 22 do not need to be controlled. Accordingly, in the present embodiment, the water-chamber working apparatus 1 includes the extrusion spring 22.

Figure 3:
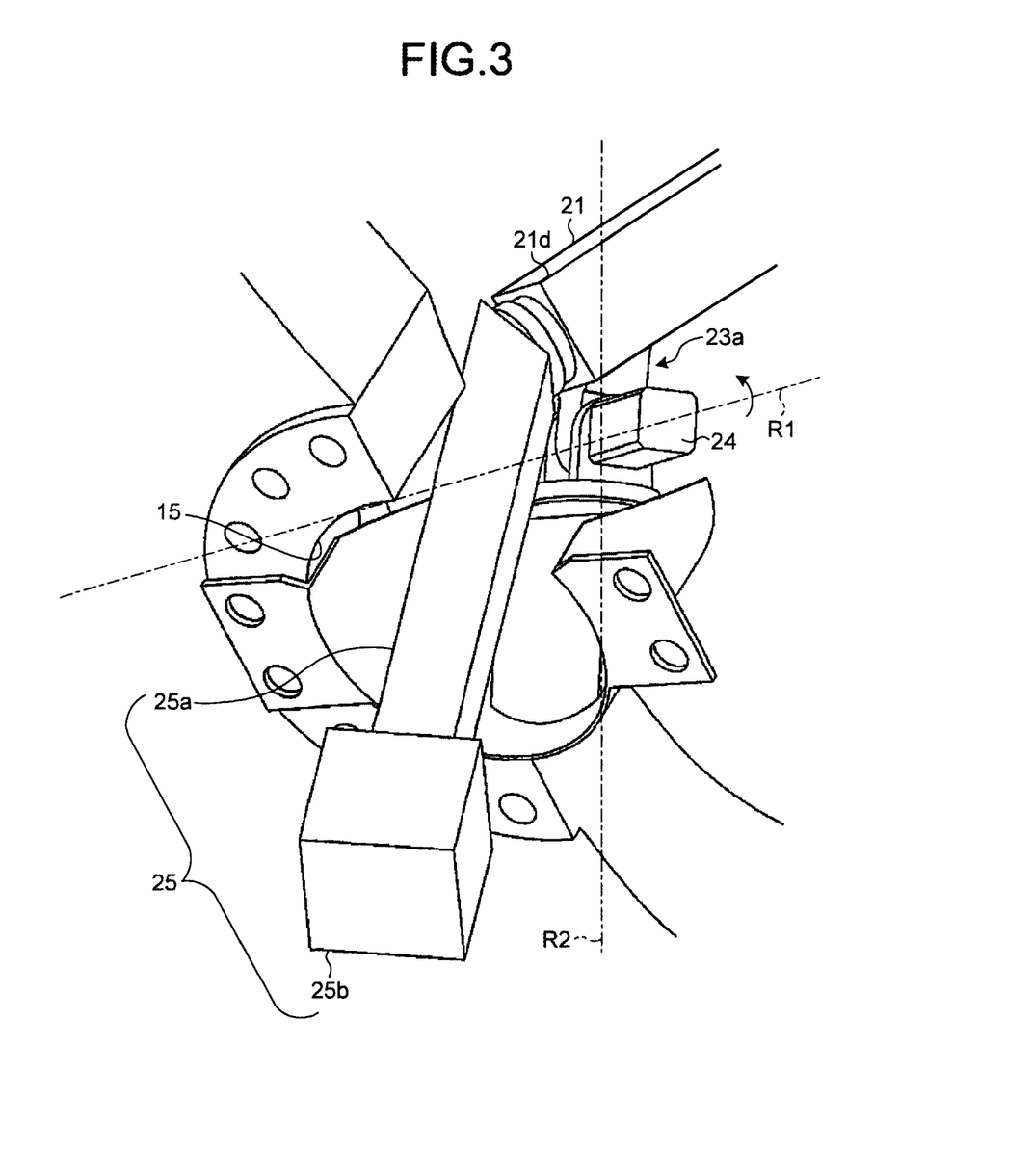
FIG. 3 is an enlarged perspective view of a vicinity of a maintenance hatch in a movable-body support device according to the first embodiment.

FIG. 3 is an enlarged perspective view of a vicinity of a maintenance hatch in the movable-body support device according to the first embodiment. As shown in FIG. 3, the first universal joint 23*a* has two rotation axes of a first rotation axis R1 and a second rotation axis R2. The first universal joint 23*a* supports the extendable member 21 with respect to the maintenance hatch 15 so that the extendable member 21 can be rotated around the first rotation axis R1. Furthermore, the first universal joint 23*a* supports the extendable member 21 with respect to the maintenance hatch 15 so that the extendable member 21 can be rotated around the second rotation axis R2. The first rotation axis R1 and the second rotation axis R2 intersect with each other. The first rotation axis R1 and the second rotation axis R2 can intersect with each other on one virtual plane or three-dimensionally. In the present embodiment, it is assumed that the first rotation axis R1 and the second rotation axis R2 intersect with each other on one virtual plane. Further, while the intersecting angle of the first rotation axis R1 and the second rotation axis R2 is not particularly limited, in the present embodiment, it is assumed that the intersecting angle is 90 degrees. Further, in the present embodiment, the first rotation axis R1 is, for example, parallel to the tube plate 12 shown in FIG. 1.

The second universal joint 23*b* shown in FIG. 2 has two rotation axes of a first rotation axis R3 and a second rotation axis R4. The second universal joint 23*b* couples the extendable member 21 with the movable body 31 so that the extendable member 21 can be rotated around the first rotation axis R3 with respect to the movable body 31. Furthermore, the second universal joint 23*b* couples the extendable member 21 with the movable body 31 so that the extendable member 21 can be rotated around the second rotation axis R4. The first rotation axis R3 and the second rotation axis R4 intersect with each other. The first rotation axis R3 and the second rotation axis R4 can intersect with each other on one virtual plane or three-dimensionally. In the present embodiment, it is assumed that the first rotation axis R3 and the second rotation axis R4 intersect with each other on one virtual plane. Further, while the intersecting angle of the first rotation axis R3 and the second rotation axis R4 is not particularly limited, in the present embodiment, it is assumed that the intersecting angle is 90 degrees. Further, in the present embodiment, the first rotation axis R3 is, for example, parallel to the tube plate 12 shown in FIG. 1.

The supporting electric motor 24 shown in FIGS. 1 and 3 applies a force of rotating the extendable member 21 around the first universal joint 23*a* as a fulcrum, which is a force in a direction in which the second coupling portion 21*e* of the extendable member 21 shown in FIG. 1 approaches the tube plate 12, to the extendable member 21. Specifically, in the supporting electric motor 24, as shown in FIG. 3, a rotor that rotates on the first rotation axis R1 is coupled with a member on a side of the extendable member 21 and a stator is coupled with a member on a side of the maintenance hatch 15. With this configuration, when the rotor rotates on the first rotation axis R1, the supporting electric motor 24 applies a force in a direction in which the second coupling portion 21*e* approaches the tube plate 12 to the extendable member 21.

Accordingly, the movable-body support device 20 presses the movable body 31 coupled with the second coupling portion 21e toward the tube plate 12 via the extendable member 21.

As shown in FIGS. 1 and 3, the movable-body support device 20 further includes a counterweight mechanism 25 as the second force application unit. The counterweight mechanism 25 includes a rod-like member 25a for weight and a weight 25b. The rod-like member 25a for weight is coupled with the first rod-like member 21a. The rod-like member 25a for weight is extended to a direction opposite to the second coupling portion 21e shown in FIG. 1 while using the first coupling portion 21d as a fulcrum. The weight 25b is provided at a position away from the first coupling portion 21d of a portion of the rod-like member 25a for weight. A vertically downward force acts on the weight 25b due to the gravity. With this configuration, the force of rotating the extendable member 21 around the first universal joint 23a as a fulcrum, which is a force in the direction in which the second coupling portion 21e of the extendable member 21 approaches the tube plate 12, is applied to the extendable member 21 from the rod-like member 25a for weight.

The movable-body support device 20 can include at least one of the supporting electric motor 24 and the counterweight mechanism 25. That is, the movable-body support device 20 can include only the supporting electric motor 24, can include only the counterweight mechanism 25, or can include both of the supporting electric motor 24 and the counterweight mechanism 25. However, by including both of the supporting electric motor 24 and the counterweight mechanism 25, the counterweight mechanism 25 can decrease the magnitude of the force to be applied to the extendable member 21 by the supporting electric motor 24. Furthermore, the supporting electric motor 24 can decrease the magnitude of the force to be applied to the extendable member 21 by the counterweight mechanism 25.

With this configuration, the supporting electric motor 24 of the movable-body support device 20 can be further downsized by including both of the supporting electric motor 24 and the counterweight mechanism 25 as compared to a case of including only the supporting electric motor 24, because an output required for the supporting electric motor 24 is decreased. Further, the movable-body support device 20 can further decrease the mass of the weight 25b or can further decrease a distance between the weight 25b and the first coupling portion 21d by including both of the supporting electric motor 24 and the counterweight mechanism 25 as compared to a case of including only the counterweight mechanism 25.

Figure 4:
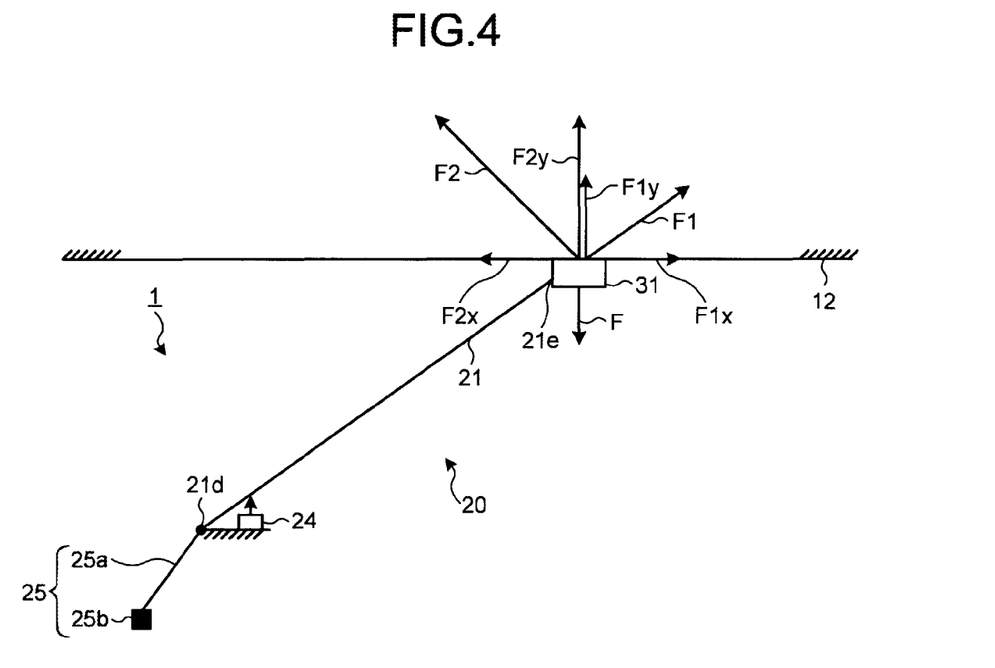
FIG. 4 is a schematic explanatory diagram of a force acting on a movable body.

FIG. 4 is a schematic explanatory diagram of a force acting on a movable body. A force F shown in FIG. 4 is the gravity acting on the movable body 31. The force F1 is generated by the extrusion spring 22 shown in FIG. 1. A force F1y is a part of the force F1 acting in a vertical direction. A force F1x is a part of the force F1 acting in a direction along the tube plate 12. A force F2 is a force transmitted to the movable body 31 via the extendable member 21 shown in FIG. 3, and is a total force of a force applied to the extendable member 21 by the supporting electric motor 24 and a force applied to the extendable member 21 by the counterweight mechanism 25. A force F2y is a part of the force F2 acting in the vertical direction. A force F2x is a part of the force F2 acting in a direction along the tube plate 12.

As shown in FIG. 4, the force F1y and the force F2y act on the movable body 31. When an angle formed by the extendable member 21 and the tube plate 12 changes, the force F1y and the force F2y respectively change. In the movable-body support device 20, the force F1 and the force F2 are adjusted in advance so that the total of the forces F1y and F2y becomes larger than the force F, at any angle of assumed angles formed by the extendable member 21 and the tube plate 12. That is, in the movable-body support device 20, a spring coefficient of the extrusion spring 22 shown in FIG. 1, an output of the supporting electric motor 24, the mass of the weight 25b, and the distance between the weight 25b and the first coupling portion 21d are adjusted in advance so that the total of the forces F1y and F2y is larger than the force F at all times.

A force of a difference between the force F1x and the force F2x acts on the movable body 31 as a force in a direction along the tube plate 12. The force in the direction along the tube plate 12 is not a force for supporting the movable body 31 on the tube plate 12. Therefore, the force in the direction along the tube plate 12 is an unnecessary force. Accordingly, it is desired that a difference between the force F1x and the force F2x is small. However, the movable body 31 according to the present embodiment can regulate the movement of the frame 33 along the tube plate 12. Therefore, even when the force in the direction along the tube plate 12 acts on the frame 33, the movable body 31 can regulate the movement of the frame 33 (can maintain suspending of the frame 33). The wheel 34 transmits a force larger than the force along the tube plate 12 acting on the frame 33 via the extendable member 21 to the tube plate 12, thereby enabling to move the movable body 31 in a direction opposite to a direction of application of the force along the tube plate 12 acting on the frame 33 via the extendable member 21.

A force directed vertically upward (the force F1y+the force F2y) acts on the movable body 31 while the extrusion spring 22 generates the force F1 and the supporting electric motor 24 and the counterweight mechanism 25 generate the force F2. This force (the force F1y+the force F2y) is larger than the gravity acting on the movable body 31. Therefore, the movable body 31 is pressed toward the tube plate 12 vertically upward. In this state, when the wheel 34 shown in FIG. 2 rotates, the frame 33 of the movable body 31 moves along the tube plate 12 against the force F1x and the force F2x shown in FIG. 4. When the movable body 31 moves, the extendable member 21 extends or retracts to follow the movement of the movable body 31. At this time, the force directed vertically upward (the force F1y+the force F2y) acts on the movable body 31. Accordingly, the movable body 31 is pressed toward the tube plate 12 vertically upward at all times. In this manner, the movable body 31 can move along the tube plate 12 without being suspended from the tube plate 12.

As described above, because the movable body 31 is not suspended from the tube plate 12, a mechanism for clamping the heat transfer tubes 14 shown in FIG. 1 does not need to be provided. Furthermore, in a mode in which the movable body is suspended from the tube plate 12, the movable body 31 needs to be operated carefully so as not to fall. On the other hand, in the present embodiment, a vertically upward force acts on the frame 33 of the movable body 31 at all times. Accordingly, the movable body 31 according to the present embodiment can stably move along the tube plate 12. As a result, if the water-chamber working apparatus includes a movable body being suspended from the tube plate 12, the water-chamber working apparatus 1 can easily operate the movable body 31.

Furthermore, the water-chamber working apparatus 1 according to the present embodiment also has a feature that if the spring coefficient of the extrusion spring 22, the output of the supporting electric motor 24, the mass of the weight 25b, and the distance between the weight 25b and the first coupling portion 21d are adjusted, the water-chamber working apparatus 1 according to the present embodiment does not need to adjust these values during a work. As described above, the total force of the force F1y and the force F2y shown in FIG. 4 is set to be larger than the force F at any angle of assumed angles formed by the extendable member 21 and the tube plate 12. Therefore, even when the movable body 31 moves along the tube plate 12, the movable body 31 is pressed against the tube plate 12 at all times. Accordingly, the water-chamber working apparatus 1 does not require any controller that controls operations of the movable-body support device 20.

(Second Embodiment)

Figure 5:
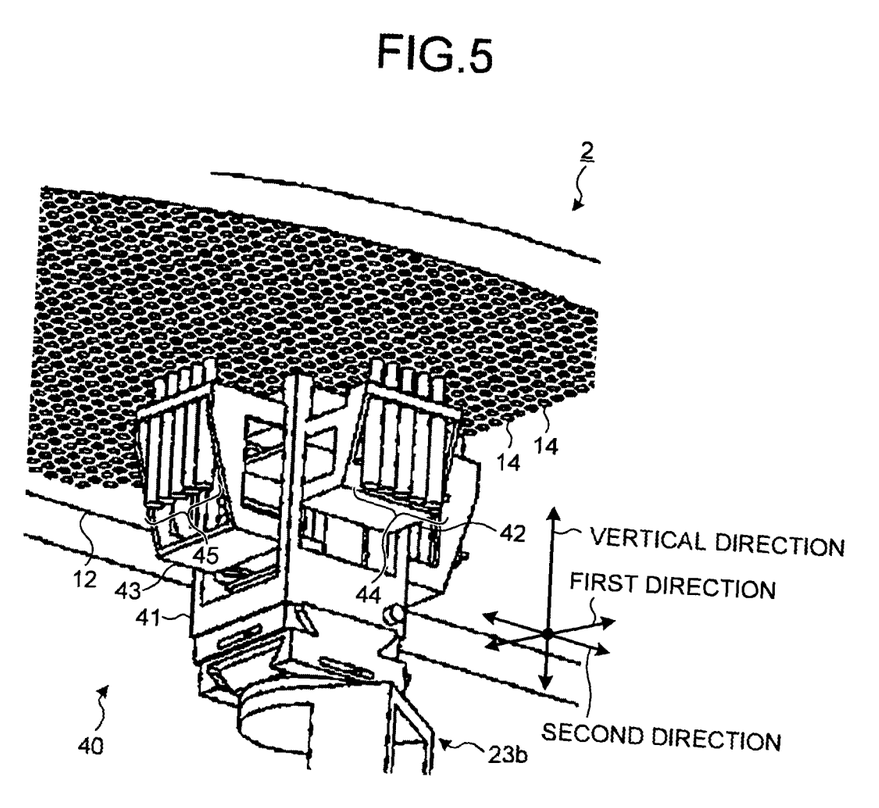
FIG. 5 is an enlarged perspective view of a vicinity of a movable body according to a second embodiment.

FIG. 5 is an enlarged perspective view of a vicinity of a movable body according to a second embodiment. In a water-chamber working apparatus 2 according to the second embodiment shown in FIG. 5, the configuration of the movable body is different from that of the water-chamber working apparatus 1 according to the first embodiment shown in FIG. 1. The configuration other than the movable body of the water-chamber working apparatus 2 is identical to that of the water-chamber working apparatus 1 according to the first embodiment. In the following explanations, a direction on a virtual plane parallel to the tube plate 12 is designated as a first direction, and a direction orthogonal to the first direction is designated as a second direction. A movable body 40 shown in FIG. 5 includes a frame 41, a first movable portion 42, a second movable portion 43, a first thruster 44, and a second thruster 45.

The frame 41 is coupled with the second coupling portion 21e of the extendable member 21 via the second universal joint 23b. The first movable portion 42 is attached to the frame 41 so as to be able to move in the first direction with respect to the frame 41. The second movable portion 43 is attached to the frame 41 so as to be able to move in the second direction with respect to the frame 41. The first thruster 44 is attached to the first movable portion 42 with a longitudinal direction thereof being the vertical direction. Furthermore, the first thruster 44 is attached to the first movable portion 42 so as to be able to move vertically upward and downward. The second thruster 45 is attached to the second movable portion 43 with a longitudinal direction thereof being the vertical direction. Further, the second thruster 45 is attached to the second movable portion 43 so as to be able to move vertically upward and downward.

A specific example of a moving method of the movable body 40 is explained below. It is assumed that before start to move, both of the first thruster 44 and the second thruster 45 of the movable body 40 are inserted into the heat transfer tubes 14. When the movable body 40 is going to move in the first direction, the second thruster 45 of the movable body 40 is first moved vertically downward. Accordingly, the engagement between the second thruster 45 and the heat transfer tubes 14 is released. The first movable portion 42 then attempts to move in the first direction. At this time, the first movable portion 42 cannot move in the first direction because the first thruster 44 is inserted into the heat transfer tubes 14. Therefore, the frame 41 and the second thruster 45 move in the first direction. The second thruster 45 then moves vertically upward and engages with the heat transfer tubes 14. Accordingly, the movable body 40 finishes the movement in the first direction.

On the other hand, when the movable body 40 is going to move in the second direction, the first thruster 44 is first moved vertically downward. Accordingly, the engagement between the first thruster 44 and the heat transfer tubes 14 is released. The second movable portion 43 then attempts to move in the second direction. At this time, the second movable portion 43 cannot move in the second direction because the second thruster 45 is inserted into the heat transfer tubes 14. Therefore, the frame 41 and the first thruster 44 move in the second direction. The first thruster 44 then moves vertically upward and engages with the heat transfer tubes 14. Accordingly, the movable body 40 completes the movement in the second direction.

The water-chamber working apparatus 2 including the movable body 40 also exhibits identical effects to those of the water-chamber working apparatus 1 according to the first embodiment shown in FIG. 1. In addition, the water-chamber working apparatus 2 according to the present embodiment shown in FIG. 5 also exhibits an effect such that positioning of the movable body 40 is easier than the movable body 31 shown in FIG. 2. In the case of the movable body 31 including the wheel 34 shown in FIG. 2, adjustment of a rotation angle of the wheel 34 and a running direction of the frame 33 needs to be accurately performed so that the probe 38 and the heat transfer tube 14 are at opposite positions. However, because the movable body 40 according to the present embodiment can perform positioning of the movable body 40 by inserting the first thruster 44 and the second thruster 45 into the heat transfer tubes 14, the probe 38 and the heat transfer tube 14 can be easily made to face each other than the movable body 31 according to the first embodiment.

As a device similar to the movable body 40 according to the present embodiment, there is a device in which a first thruster and a second thruster clamp the heat transfer tubes 14. However, the movable body 40 according to the present embodiment is pressed against the tube plate 12 by the movable-body support device 20. Therefore, the first thruster 44 and the second thruster 45 of the movable body 40 do not need to clamp the heat transfer tubes 14. Accordingly, because a clamping work of the heat transfer tubes 14 by the first thruster 44 and the second thruster 45 is not required, the movable body 40 can move more quickly along the tube plate 12.

However, the movable body 31 according to the first embodiment and the movable body 40 according to the second embodiment can include a mechanism for clamping the heat transfer tubes 14 (hereinafter, "clamping mechanism"). In this case, the movable-body support device exhibits a new effect. The effect is explained below. When the water-chamber working apparatus 1 performs Eddy-current testing, the movable body receives a force in a direction in which the movable body itself moves away from the heat transfer tubes 14 (a reaction force) from the probe 38. Accordingly, when the movable body does not include the clamping mechanism, at least one of the supporting electric motor 24 and the counterweight mechanism 25 of the movable-body support device needs to generate a force against the reaction force. However, when the movable body includes the clamping mechanism, the movable body is fixed to the tube plate 12 by the clamping mechanism. Therefore, at least one of the supporting electric motor 24 and the counterweight mechanism 25 of the movable-body support device do not need to generate the force against the reaction force. Accordingly, at least one of the supporting electric motor 24 and the counterweight mechanism 25 of the movable-body support device can be downsized.

(Third Embodiment)

Figure 6:
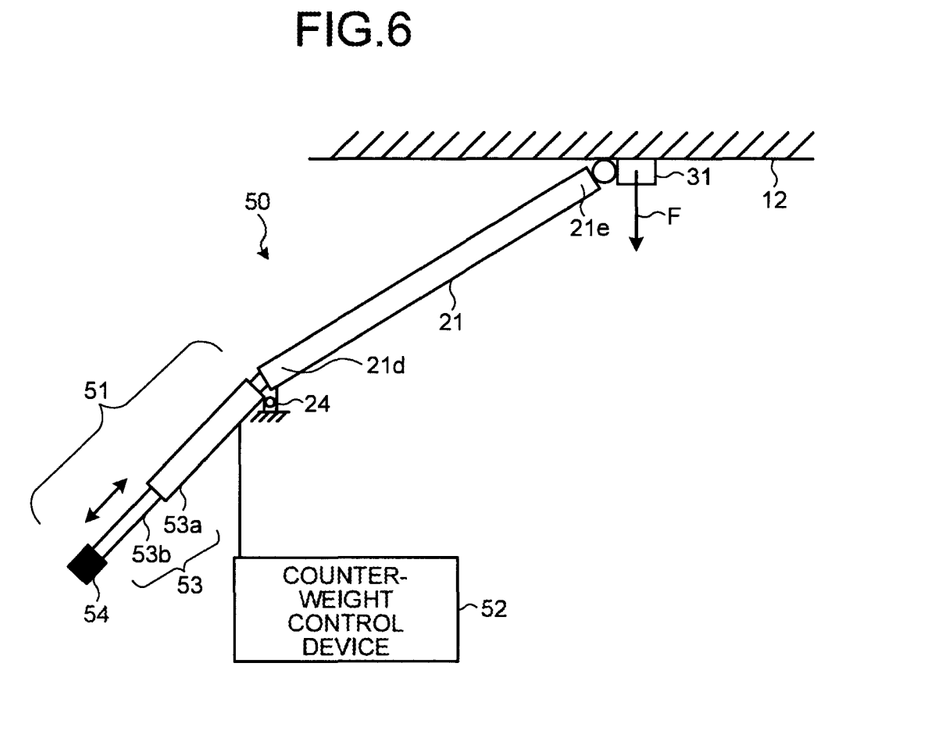
FIG. 6 is an explanatory diagram of a counterweight mechanism according to a third embodiment.

FIG. 6 is an explanatory diagram of a counterweight mechanism according to a third embodiment. A movable-body support device 50 according to the third embodiment includes, as shown in FIG. 6, a counterweight mechanism 51 as the second force application unit, and a counterweight control device 52. The counterweight mechanism 51 includes a cylinder device 53 as an arm-length adjustment unit and a weight 54. The cylinder device 53 operates by using, for example, gas or liquid as a working fluid. The cylinder device 53 includes a first member 53a and a second member 53b that protrudes from the first member 53a due to pressure of the working fluid. The weight 54 is provided in the second member 53b. The counterweight control device 52 adjusts a flow rate of the working fluid conducted to the cylinder device 53 and controls a protrusion amount of the second member 53b from the first member 53a. As a result, the counterweight control device 52 adjusts the distance between the weight 54 and the first coupling portion 21d.

When the distance between the weight 54 and the first coupling portion 21d changes, the magnitude of the force F2 shown in FIG. 4 changes. Specifically, when the distance between the weight 54 and the first coupling portion 21d increases, the force F2 shown in FIG. 4 increases, and when the distance between the weight 54 and the first coupling portion 21d decreases, the force F2 shown in FIG. 4 decreases. On the other hand, as the distance between the first coupling portion 21d and the second coupling portion 21e increases, that is, the length of the extendable member 21 increases, a force required for pressing the movable body 31 against the tube plate 12 increases in the movable-body support device 50. Furthermore, in the movable-body support device 50, as the length of the extendable member 21 decreases, the force required for pressing the movable body 31 against the tube plate 12 decreases.

Accordingly, as the length of the extendable member 21 increases, the counterweight control device 52 increases the protrusion amount of the second member 53b from the first member 53a to increase the distance between the weight 54 and the first coupling portion 21d. With this configuration, in the movable-body support device 50, the counterweight mechanism 51 can preferably decrease a load of the supporting electric motor 24. As the length of the extendable member 21 decreases, the counterweight control device 52 decreases the protrusion amount of the second member 53b from the first member 53a to decrease the distance between the weight 54 and the first coupling portion 21d. Accordingly, the movable-body support device 50 can reduce the possibility that a vertically upward force acts on the movable body 31 more than necessary.

(Fourth Embodiment)

Figure 7:
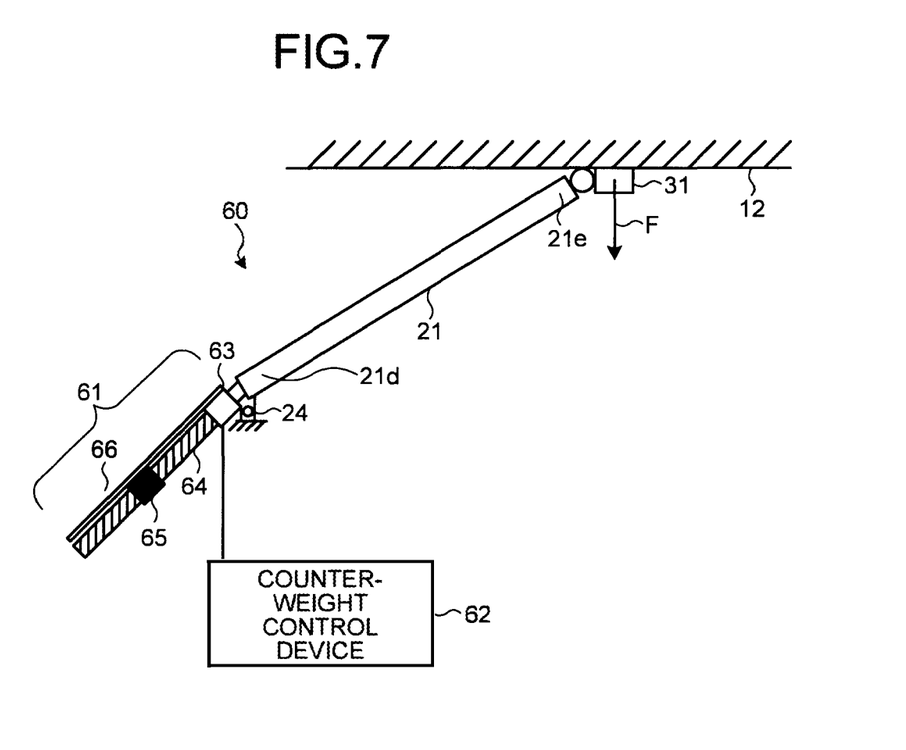
FIG. 7 is an explanatory diagram of a counterweight mechanism according to a fourth embodiment.

FIG. 7 is an explanatory diagram of a counterweight mechanism according to a fourth embodiment. A movable-body support device 60 according to the fourth embodiment shown in FIG. 7 is similar to the movable-body support device 50 according to the third embodiment shown in FIG. 6 in that the distance between the weight and the first coupling portion can be adjusted. The movable-body support device 60 includes a counterweight mechanism 61 as the second force application unit, and a counterweight control device 62. The counterweight mechanism 61 includes a weight movement unit and a weight 65. The weight movement unit is configured to include a screw-rotating electric motor 63, an external-thread rotating shaft 64, and a weight-rotation regulating member 66. The screw-rotating electric motor 63 rotates the external-thread rotating shaft 64 on a central axis of the external-thread rotating shaft 64. The weight 65 is a nut-like member, and an internal thread is formed on an inner periphery of a cylinder. The weight 65 is screwed together with the external-thread rotating shaft 64. The weight-rotation regulating member 66 regulates rotation of the weight 65 so that the weight 65 does not rotate together with the external-thread rotating shaft 64 when the external-thread rotating shaft 64 is rotated. In the counterweight mechanism 61, when the external-thread rotating shaft 64 is rotated, the weight 65 moves along the external-thread rotating shaft 64.

The counterweight control device 62 is electrically connected to the screw-rotating electric motor 63. The counterweight control device 62 controls operations of the screw-rotating electric motor 63 to adjust a rotation direction and a rotation amount of the external-thread rotating shaft 64. As the length of the extendable member 21 increases, the counterweight control device 62 rotates the external-thread rotating shaft 64 in one direction to increase the distance between the weight 65 and the first coupling portion 21d. With this configuration, in the movable-body support device 60, the counterweight mechanism 61 can decrease a load of the supporting electric motor 24 more preferably. Furthermore, as the length of the extendable member 21 decreases, the counterweight control device 62 rotates the external-thread rotating shaft 64 in a direction opposite to the direction described above, to decrease the distance between the weight 65 and the first coupling portion 21d. Accordingly, the movable-body support device 60 can reduce the possibility that a vertically upward force acts on the movable body 31 more than necessary.

(Fifth Embodiment)

Figure 8:
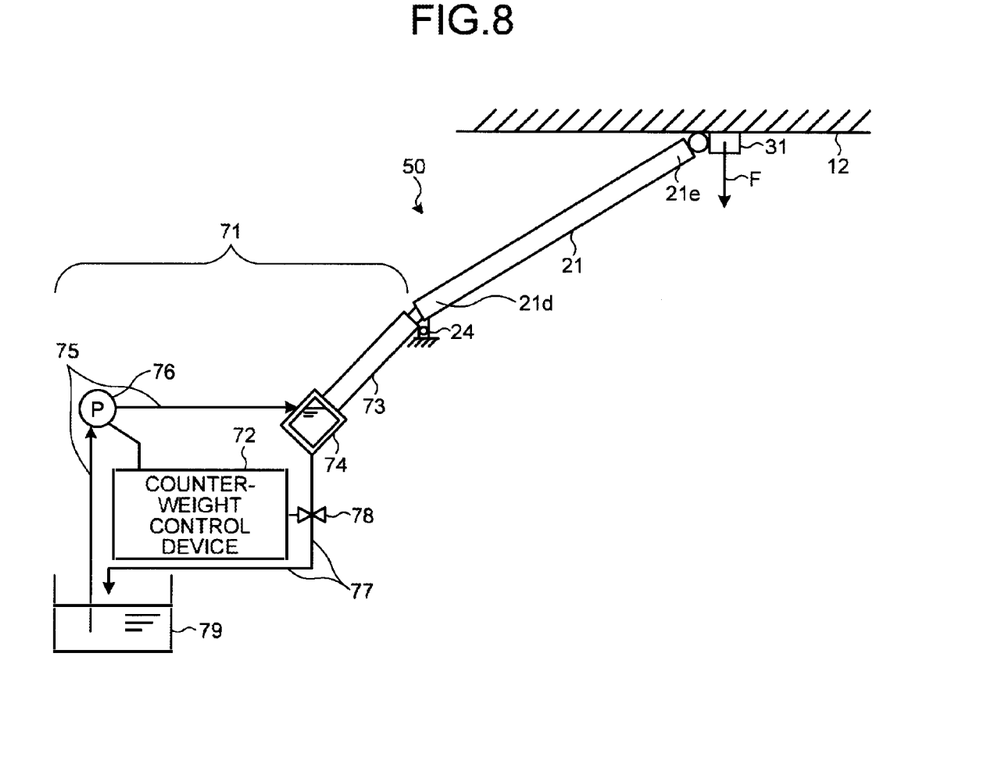
FIG. 8 is an explanatory diagram of a counterweight mechanism according to a fifth embodiment.

FIG. 8 is an explanatory diagram of a counterweight mechanism according to a fifth embodiment. A movable-body support device 70 according to the fifth embodiment shown in FIG. 8 has a feature that the mass of a weight is changed. The movable-body support device 70 includes a counterweight mechanism 71 as the second force application unit and a counterweight control device 72. The counterweight mechanism 71 includes a rod-like member 73 for weight, a container 74, and a fluid-amount adjustment unit. The fluid-amount adjustment unit is configured to include a fluid supply path 75, a pump 76, a fluid discharge path 77, a solenoid valve 78, and a tank 79. The rod-like member 73 for weight is connected to the extendable member 21. Specifically, the rod-like member 73 for weight is extended to an opposite side to the second coupling unit 21e while using the first coupling unit 21d as a fulcrum. The container 74 is provided at a portion of the rod-like member 73 for weight that is away from the first coupling unit 21d. One end of the fluid supply path 75 and of the fluid discharge path 77 respectively opens to the container 74, and the other end thereof opens to the tank 79. The pump 76 is provided in the fluid supply path 75 and guides a fluid stored in the tank 79 to the container 74. The solenoid valve 78 is provided in the fluid discharge path 77. The solenoid valve 78 guides a fluid in the container 74 to the tank 79 at the time of being opened, and stores the fluid in the container 74 at the time of being closed. In the movable-body support device 70, the mass of the container 74 containing liquid changes according to the fluid volume of the fluid in the container 74.

The counterweight control device 72 is electrically connected to the pump 76 and the solenoid valve 78. The counterweight control device 72 controls operations of the pump 76 to adjust the flow rate of the liquid guided into the container 74. Furthermore, the counterweight control device 72 controls opening and closing of the solenoid valve 78 to adjust the flow rate of the liquid to be discharged from the container 74. In this manner, the counterweight control device 72 adjusts the fluid volume of the liquid in the container 74. The counterweight control device 72 increases the fluid volume of the liquid in the container 74 as the length of the extendable member 21 increases. With this configuration, a vertically upward force acting on the movable body 31 and generated by the counterweight mechanism 71 increases. Therefore, in the movable-body support device 70, the counterweight mechanism 71 can decrease a load of the supporting electric motor 24 more preferably. Furthermore, the counterweight control device 72 decreases the fluid volume of the liquid in the container 74 as the length of the extendable member 21 decreases. With this configuration, the vertically upward force acting on the movable body 31 and generated by the counterweight mechanism 71 decreases. Accordingly, the movable-body support device 70 can reduce the possibility that the vertically upward force acts on the movable body 31 more than necessary.

While each of the movable-body support devices according to the third to fifth embodiments adjusts the magnitude of the force F2 generated by the counterweight mechanism, the movable-body support device can adjust the magnitude of the force F2 generated by the supporting electric motor 24. In this case, the movable-body support device includes a supporting electric-motor controller. As the distance between the first coupling unit 21d and the second coupling unit 21e increases, that is, as the length of the extendable member 21 increases, the supporting electric-motor controller increases the magnitude of the force F2 generated by the supporting electric motor 24. Furthermore, as the length of the extendable member 21 decreases, the supporting electric-motor controller decreases the magnitude of the force F2 generated by the supporting electric motor 24. Also in this mode, the movable-body support device can reduce the possibility that the vertically upward force acts on the movable body 31 more than necessary.

INDUSTRIAL APPLICABILITY

As described above, the water-chamber working apparatus according to the present invention is useful for a technique of performing a predetermined work in a water chamber of a steam generator, and is particularly suitable for stably supporting a movable body on a tube plate.

REFERENCE SIGNS LIST 1, 2 water-chamber working apparatus
10 steam generator
11 water chamber
12 tube plate
13 hemispherical wall surface
14 heat transfer tube
15 maintenance hatch
20, 50, 60, 70 movable-body support device
21 extendable member
21a first rod-like member
21b second rod-like member
21c third rod-like member
21d first coupling portion (first portion)
21e second coupling portion (second portion)
22 extrusion spring (first force application unit)
23a first universal joint
23b second universal joint
24 supporting electric motor (second force application unit)
25, 51, 61, 71 counterweight mechanism (second force application unit)
25a, 73 rod-like member for weight
25b, 54, 65 weight
30 flaw detector
31, 40 movable body
32 movable-body control device
33, 41 frame
34 wheel
35 running electric motor
36 running-direction-changing electric motor
37 probe support body
38 probe
42 first movable portion
43 second movable portion
44 first thruster
45 second thruster
52, 62, 72 counterweight control device
53 cylinder device (arm-length adjustment unit)
53a first member
53b second member
63 screw-rotating electric motor (weight movement unit)
64 external-thread rotating shaft (weight movement unit)
66 weight-rotation regulating member (weight movement unit)
74 container
75 fluid supply path (fluid-amount adjustment unit)
76 pump (fluid-amount adjustment unit)
77 fluid discharge path (fluid-amount adjustment unit)
78 solenoid valve (fluid-amount adjustment unit)
79 tank (fluid-amount adjustment unit)
R1, R3 first rotation axis
R2, R4 second rotation axis

The invention claimed is:

1. A water-chamber working apparatus that performs a predetermined work inside a water chamber of a steam generator, the apparatus comprising:
a movable body that is configured to move along a tube plate of the steam generator;
an extendable member that includes a first portion and a second portion and that extends and retracts in a direction in which the first portion and the second portion approach each other and a direction in which theses portions move away from each other, where the first portion is attached to a portion of the water chamber that is away from the tube plate via a first joint including two rotation axes intersecting with each other, and the second portion is attached to the movable body via a second joint including two rotation axes intersecting with each other, which are different from the rotation axes of the first joint;
a first force application unit that applies a force in a direction in which the first portion and the second portion move away from each other to the extendable member; and
a second force application unit that applies a force of rotating the extendable member centering around the first joint, which is a force to cause the second portion to approach to the tube plate, to the extendable member.

2. The water-chamber working apparatus according to claim 1, wherein
the second force application unit includes
an electric motor, and
a counterweight mechanism including a rod-like member for weight that is extended to a direction opposite to the second portion while using the first portion as a fulcrum, and a weight provided in a portion of the rod-like member for weight that is away from the first portion.

3. The water-chamber working apparatus according to claim 2, wherein the electric motor increases the force to be applied to the extendable member as a distance between the first portion and the second portion increases, and decreases the force to be applied to the extendable member as the distance between the first portion and the second portion decreases.

4. The water-chamber working apparatus according to claim 1, wherein
the second force application unit is a counterweight mechanism including
a rod-like member for weight that is extended to a direction opposite to the second portion while using the first portion as a fulcrum, and
a weight provided in a portion of the rod-like member for weight that is away from the first portion.

5. The water-chamber working apparatus according to claim 2, wherein
the rod-like member for weight extends and retracts in a direction in which the first portion and the weight approach each other and a direction in which the first portion and the weight move away from each other, and
the water-chamber working apparatus comprises an arm-length adjustment unit that adjusts a distance between the first portion and the weight so that the distance between the first portion and the weight increases as a distance between the first portion and the second portion increases, and adjusts a distance between the first portion and the weight so that the distance between the first portion and the weight decreases as the distance between the first portion and the second portion decreases.

6. The water-chamber working apparatus according to claim 2, wherein
the weight moves along the rod-like member for weight in a direction in which the weight approaches the first portion and a direction in which the weight moves away from the first portion, and
the water-chamber working apparatus comprises a weight movement unit that moves the weight in a direction in which the weight moves away from the first portion as a distance between the first portion and the second portion increases, and moves the weight in a direction in which the weight approaches the first portion as the distance between the first portion and the second portion decreases.

7. The water-chamber working apparatus according to claim 2, wherein
the weight is configured to include a container and liquid stored in the container, and
the water-chamber working apparatus comprises a liquid-amount adjustment unit that increases an amount of the liquid in the container as a distance between the first portion and the second portion increases, and decreases an amount of the liquid in the container as the distance between the first portion and the second portion decreases.

8. The water-chamber working apparatus according to claim 1, wherein the second force application unit is an electric motor.

9. The water-chamber working apparatus according to claim 8, wherein the electric motor increases the force to be applied to the extendable member as a distance between the first portion and the second portion increases, and decreases the force to be applied to the extendable member as the distance between the first portion and the second portion decreases.

10. The water-chamber working apparatus according to claim 1, wherein the first force application unit is an extension device capable of adjusting an amount of extension and retraction, and adjusts a length of the extendable member by following a movement of the movable body.

11. The water-chamber working apparatus according to claim 1, wherein the movable body performs, as a predetermined work, Eddy-current testing for probing a flaw formed in a heat transfer tube provided in the steam generator.

12. The water-chamber working apparatus according claim 11, wherein the movable body clamps the heat transfer tube.

* * * * *